(12) United States Patent
Uchimura

(10) Patent No.: US 8,517,926 B2
(45) Date of Patent: Aug. 27, 2013

(54) ENDOSCOPE

(75) Inventor: Sumihiro Uchimura, Kanagawa (JP)

(73) Assignee: Olympus Medical Systems Corp., Tokyo (JP)

( * ) Notice: Subject to any disclaimer, the term of this patent is extended or adjusted under 35 U.S.C. 154(b) by 1119 days.

(21) Appl. No.: 11/915,062

(22) PCT Filed: May 23, 2006

(86) PCT No.: PCT/JP2006/310269
§ 371 (c)(1),
(2), (4) Date: Nov. 20, 2007

(87) PCT Pub. No.: WO2006/126550
PCT Pub. Date: Nov. 30, 2006

(65) Prior Publication Data
US 2009/0048488 A1 Feb. 19, 2009

(30) Foreign Application Priority Data
May 24, 2005 (JP) ................................. 2005-151337

(51) Int. Cl.
*A61B 1/00* (2006.01)
(52) U.S. Cl.
USPC ........................... 600/152; 600/146; 600/150
(58) Field of Classification Search
USPC ................ 600/152, 144, 146, 150, 139, 145
See application file for complete search history.

(56) References Cited

U.S. PATENT DOCUMENTS

| | | | | | |
|---|---|---|---|---|---|
| 4,292,961 A | * | 10/1981 | Kawashima | .................. | 600/145 |
| 5,014,515 A | * | 5/1991 | Krauter | ............................ | 60/581 |
| 5,179,935 A | * | 1/1993 | Miyagi | ........................... | 600/142 |
| 7,041,053 B2 | * | 5/2006 | Miyake | ........................... | 600/146 |
| 7,918,790 B2 | * | 4/2011 | Ikeda et al. | .................... | 600/152 |
| 2003/0006669 A1 | | 1/2003 | Pei et al. | | |
| 2003/0071328 A1 | | 4/2003 | Boecking | | |
| 2004/0143160 A1 | * | 7/2004 | Couvillon, Jr. | ............... | 600/114 |
| 2004/0199053 A1 | * | 10/2004 | Boulais et al. | ................ | 600/146 |
| 2005/0065571 A1 | | 3/2005 | Imran | | |
| 2005/0085693 A1 | * | 4/2005 | Belson et al. | ................. | 600/146 |
| 2005/0209509 A1 | * | 9/2005 | Belson | ............................ | 600/146 |
| 2006/0258912 A1 | * | 11/2006 | Belson et al. | ................. | 600/152 |

FOREIGN PATENT DOCUMENTS

| | | |
|---|---|---|
| JP | 05 103755 A | 4/1993 |
| JP | 08 024218 A | 1/1996 |
| JP | 2003-038418 | 2/2003 |
| JP | 2004-024860 | 1/2004 |

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

An endoscope having an insertion portion including a bending portion, an actuator that extends or contracts according to application of a driving voltage and that bends the bending portion, a bending instruction operation portion for outputting, to the actuator, an instruction signal of a bending direction and a bending amount so that the bending portion performs a bending action by an arbitrary amount from a reference direction in which the bending portion is not bent to an arbitrary direction, and a control portion for performing control to apply the actuator with a driving voltage to cause the actuator to extend or contract in a predetermined direction and by a predetermined amount so that the bending portion performs a returning action in the reference direction when detecting the instruction signal outputted by the bending instruction operation portion for returning the bending portion to the reference direction.

5 Claims, 10 Drawing Sheets

(56) References Cited

FOREIGN PATENT DOCUMENTS

| JP | 2004-350495 | 12/2004 |
| JP | 2005-305047 | 11/2005 |
| WO | WO 2004/098040 | 11/2004 |
| WO | WO 2005/018428 A2 | 3/2005 |

* cited by examiner

ENDOSCOPE

TECHNICAL FIELD

The present invention relates to an endoscope including a bending portion configured of an actuator using a conductive polymer member which extends and contracts in response to application of a driving voltage.

BACKGROUND ART

Conventionally, an endoscope has been widely used in a medical field, an industrial field, and the like. For example, in the medical field, an endoscope is used when various treatments are performed on a region of body cavity in a living body, tissues, or the like, which are diseased parts.

A bending portion of an endoscope is provided with a mechanism for directing a distal end portion of the bending portion to a desired region by a bending action of the bending portion in order for an operator to surely perform various treatments when performing various treatments on the diseased part with the endoscope. Such an endoscope having the above-described mechanism is proposed in Japanese Unexamined Patent Application Publication No. 2003-38418, for example.

The bending portion of the endoscope proposed in the Japanese Unexamined Patent Application Publication No. 2003-38418 has a configuration in which a plurality of bending pieces are provided, and the shape of the bending portion is changed by advancing and retreating a bending wire with the operation of a bending portion operation knob provided in an operation portion of the endoscope.

In order to realize the configuration, a bending mechanism configured of a motor, the bending pieces, the bending wire, and the like, is required to be provided to an operation portion, an insertion portion, and the bending portion. However, providing the bending mechanism to the endoscope leads to an increase in weight of the endoscope itself and as a result, physical burden of an operator increases when performing a treatment by using the endoscope for many hours on end.

On the other hand, U.S. patent application publication No. 2003/0006669, for example, discloses a configuration in which a roll-shaped conductive polymer member is formed by winding in a cylindrical shape a thin plate-like conductive polymer having electrodes on both opposed surfaces thereof, and the part on which electrodes are provided can be bent by extending and contracting in a thickness direction with application of voltage to the electrodes opposed to each other.

In addition, the publication discloses a conductive polymer actuator ensuring a shape recovery function by providing a coil-shaped spring inside of the roll-shaped conductive polymer member.

The conductive polymer actuator has a possibility of reducing the weight of the bending mechanism and improving operability when utilized in a bending portion of an endoscope.

The operability is enhanced if responsiveness can be further improved.

The present invention has been made in view of the above-described points and an object of the present invention is to provide an endoscope capable of improving operability for changing a shape of a bending portion as well as improving responsiveness.

DISCLOSURE OF INVENTION

Means for Solving the Problem

An endoscope provided with a bending portion in an insertion portion, including: an actuator formed with a conductive polymer member that extends and contracts according to application of a driving voltage, the actuator configuring the bending portion; bending instruction operation means for performing instruction operation of a bending direction to bend the actuator from a reference direction to an arbitrary direction; and control means for performing control to generate a driving voltage for bending the actuator in a direction returning to the reference direction when detecting an instruction operation in the direction returning to the reference direction after detecting instruction operation of the bending direction by the bending instruction operation means.

BRIEF DESCRIPTION OF THE DRAWINGS

FIG. 10A is an explanatory diagram showing the case where the responsiveness according to the first embodiment is improved. FIG. 10B is an explanatory diagram showing the case where the responsiveness is not improved.

BEST MODE FOR CARRYING OUT THE INVENTION

Hereinafter, embodiments of the present invention are described with reference to the drawings.
(First Embodiment)

Figure 1:
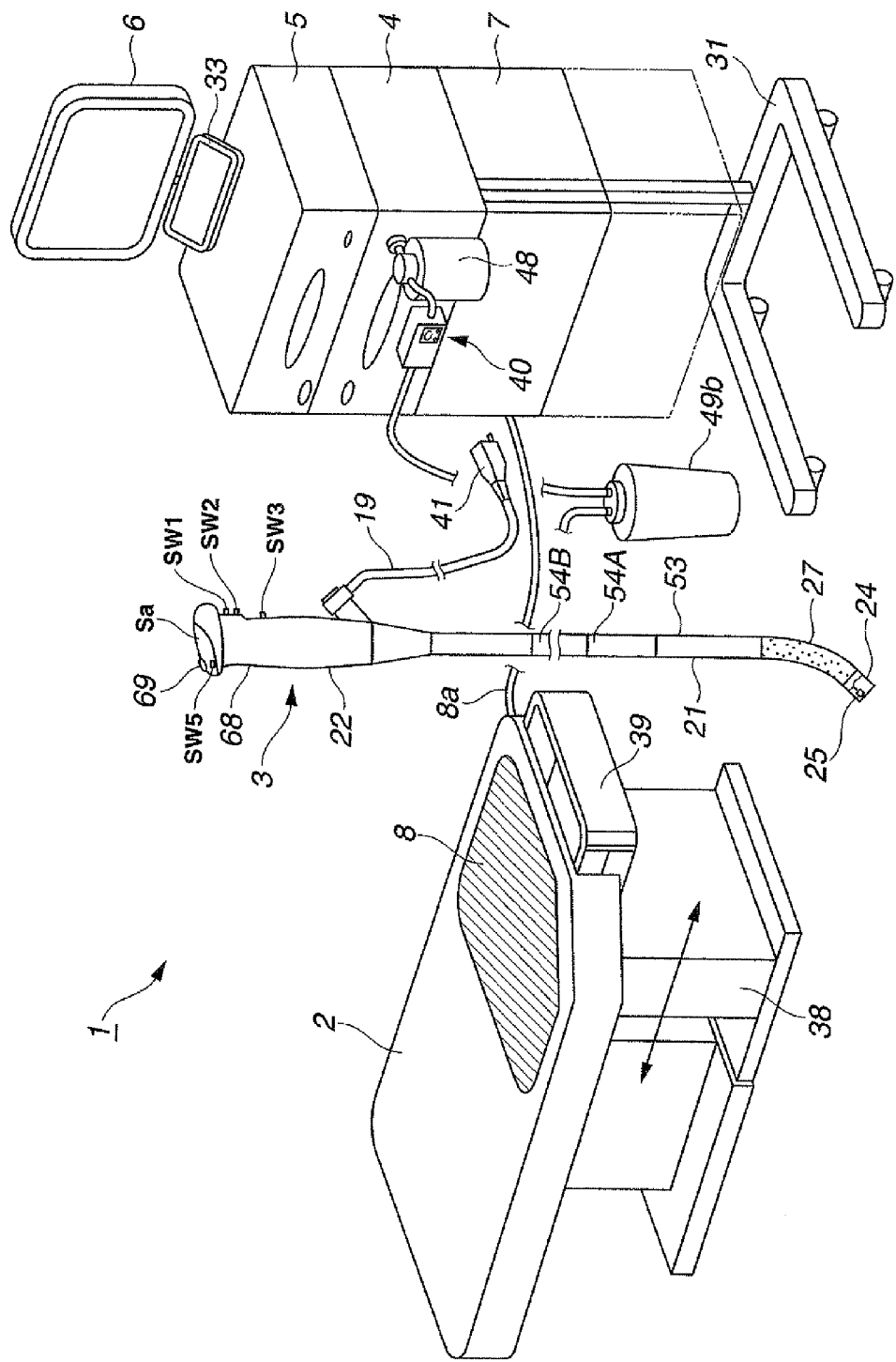
FIG. 1 is a schematic configurational diagram of an endoscope system provided with the present invention.
Figure 2:
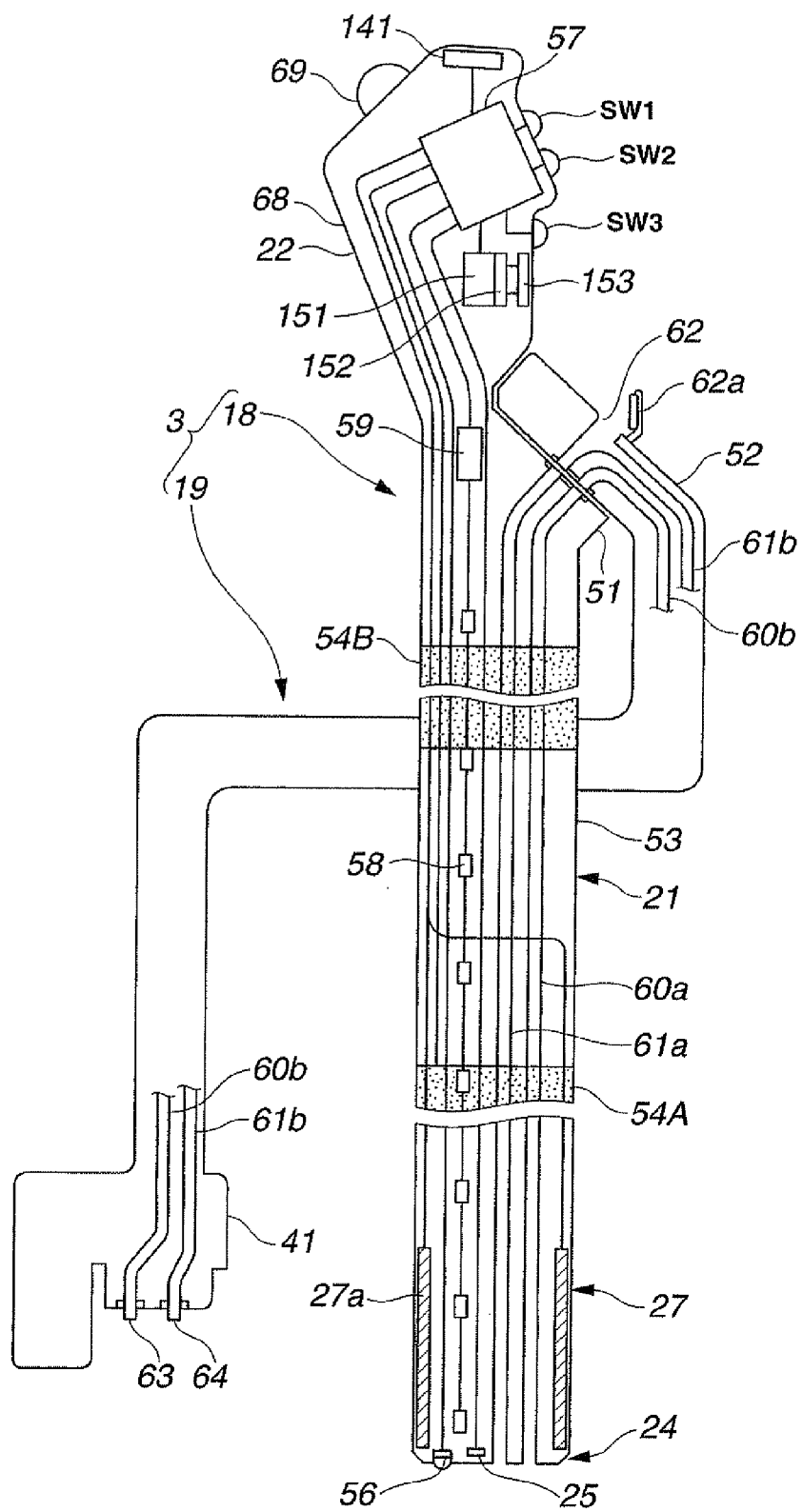
FIG. 2 is an overall diagram showing a detailed configuration of an endoscope according to a first embodiment.
Figure 3:
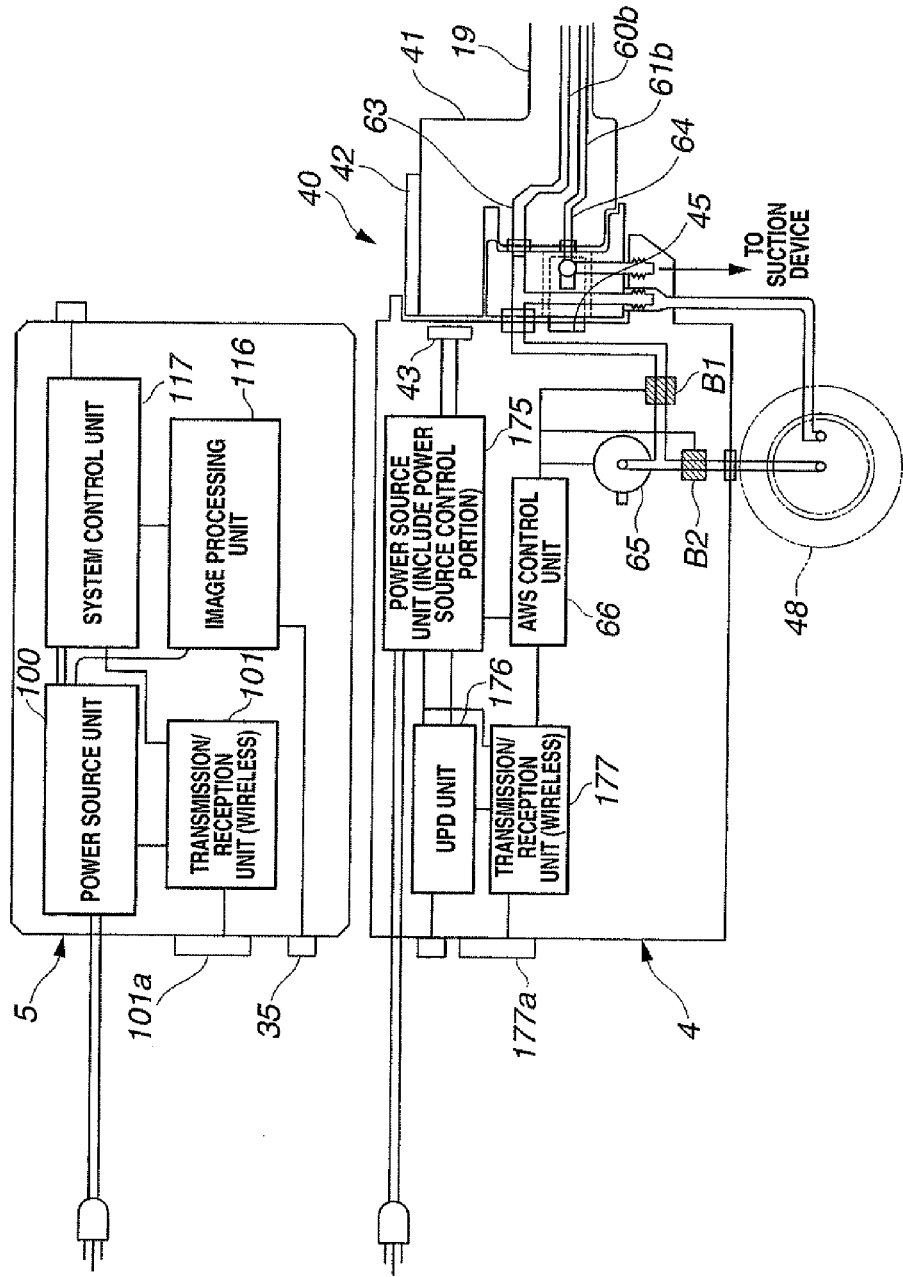
FIG. 3 is a diagram showing an inner configuration of an endoscope system control apparatus and an AWS unit, and a structure of a connection portion of a scope connector.
Figure 4:
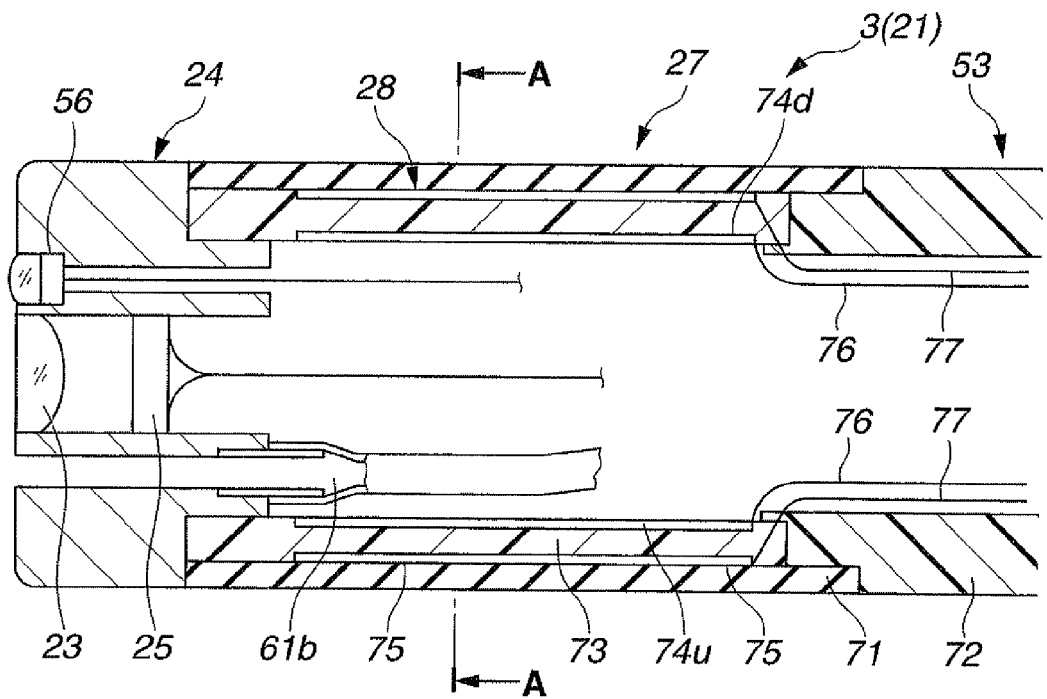
FIG. 4 is a vertical cross-sectional diagram showing an inner configuration of a distal end side of an insertion portion of the endoscope.
Figure 5:
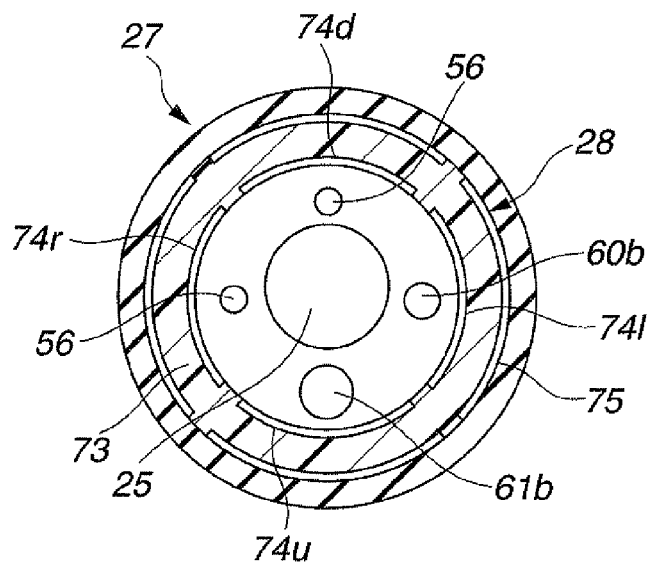
FIG. 5 is a cross-sectional diagram taken along line A-A of FIG. 4.

FIGS. 1 to 12 relate to the first embodiment of the present invention in which:

FIG. 1 shows a schematic configuration of an endoscope system provided with the first embodiment of the present invention; FIG. 2 shows an overall configuration of an endoscope according to the first embodiment; FIG. 3 shows an inner configuration of an endoscope system control apparatus and an AWS unit, and a structure of a connection portion of a scope connector; FIG. 4 shows an inner configuration of a distal end side of an insertion portion; and FIG. 5 shows a cross-sectional structure taken along line A-A of FIG. 4.

Figure 6:
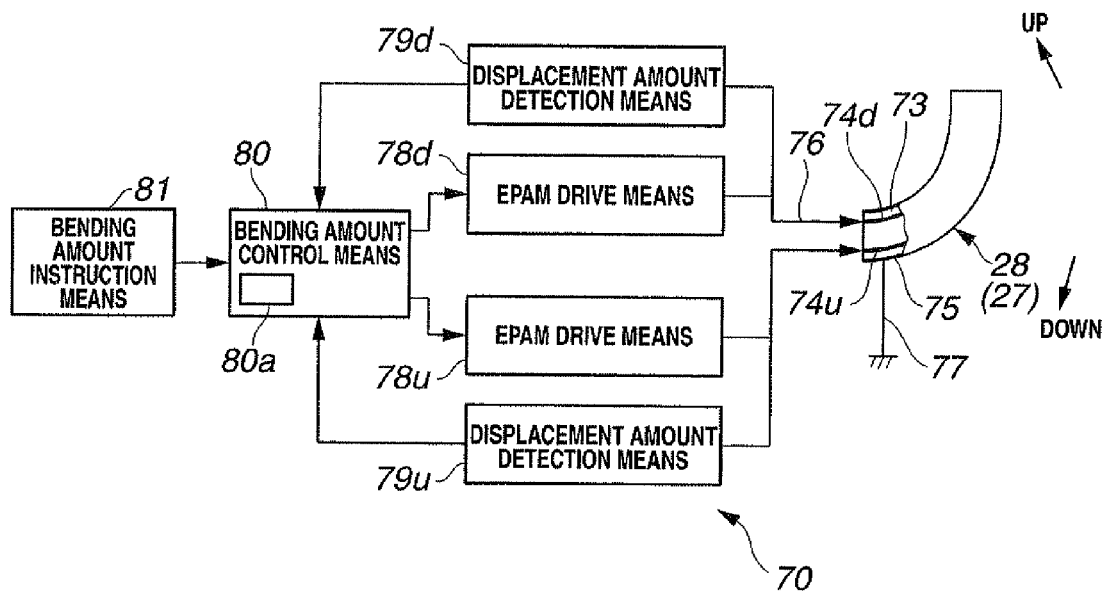
FIG. 6 is a block diagram showing a schematic configuration of a bending control mechanism according to the first embodiment.
Figure 7:
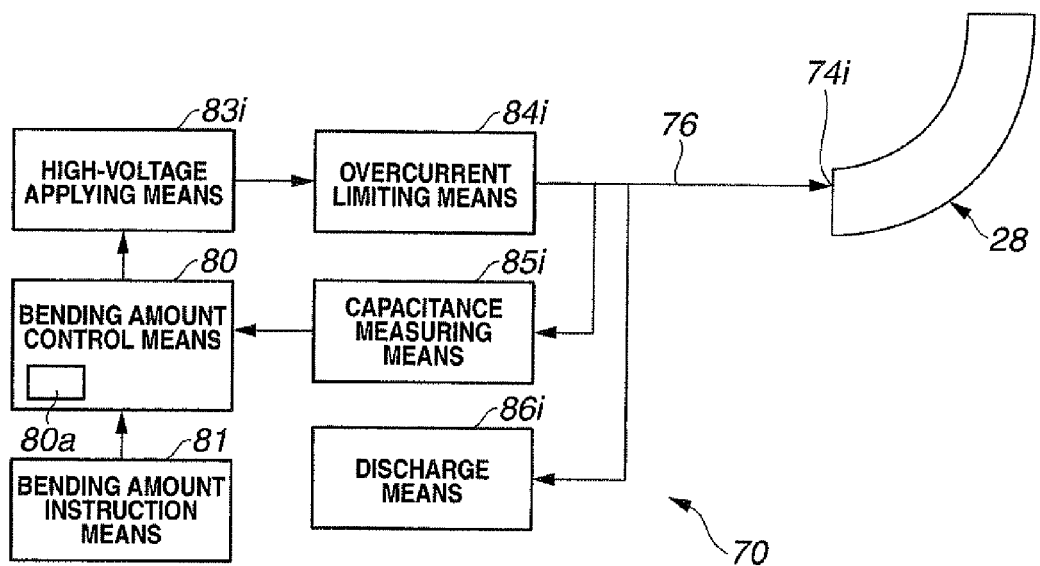
FIG. 7 is a block diagram showing a more specific configuration of FIG. 6.
Figure 8:
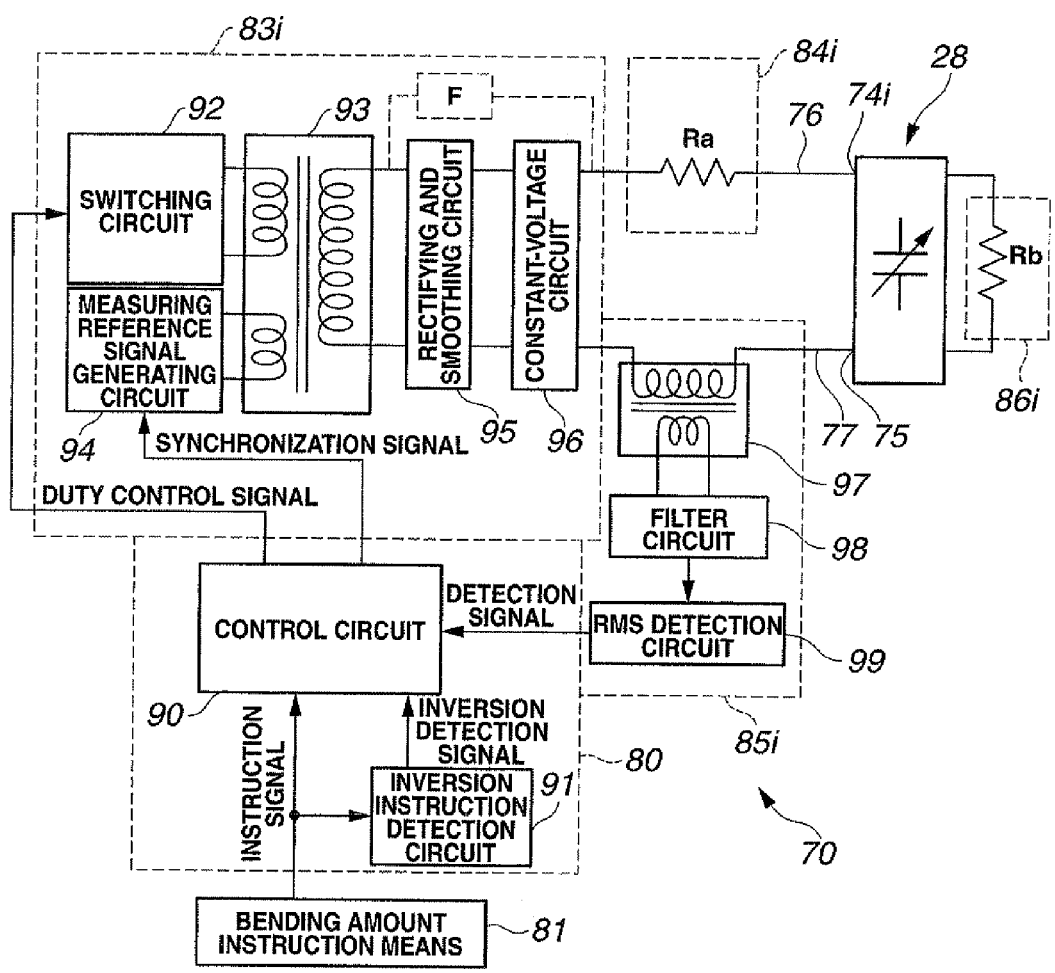
FIG. 8 is a block diagram showing a more specific configuration of FIG. 7.
Figure 9:
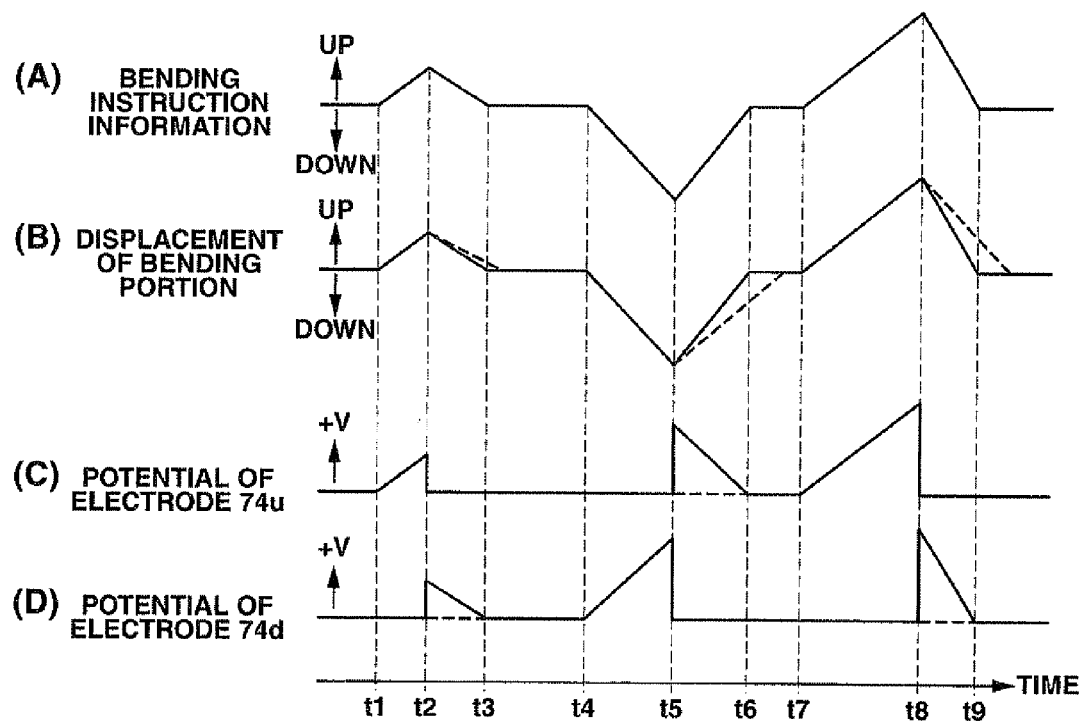
FIG. 9 is a timing chart diagram describing an action of the bending control mechanism of FIG. 6.
Figure 10A:
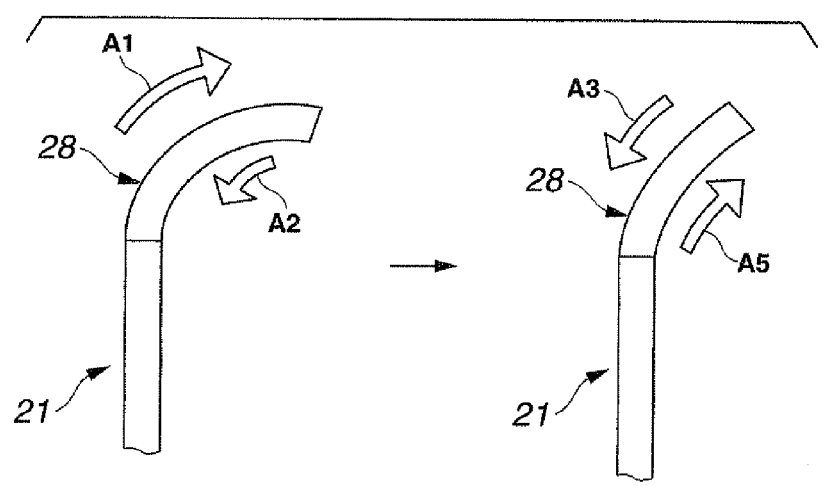
FIGS. 10A and 10B are explanatory diagrams showing a comparison of an action in a case where the responsiveness according to the first embodiment is improved and that in a case where the responsiveness is not improved.
Figure 10B:
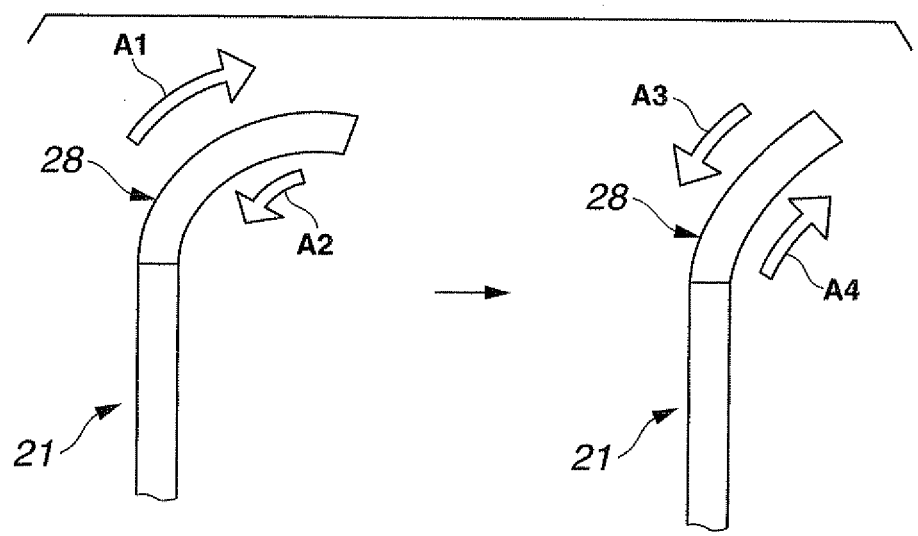
Figure 11:
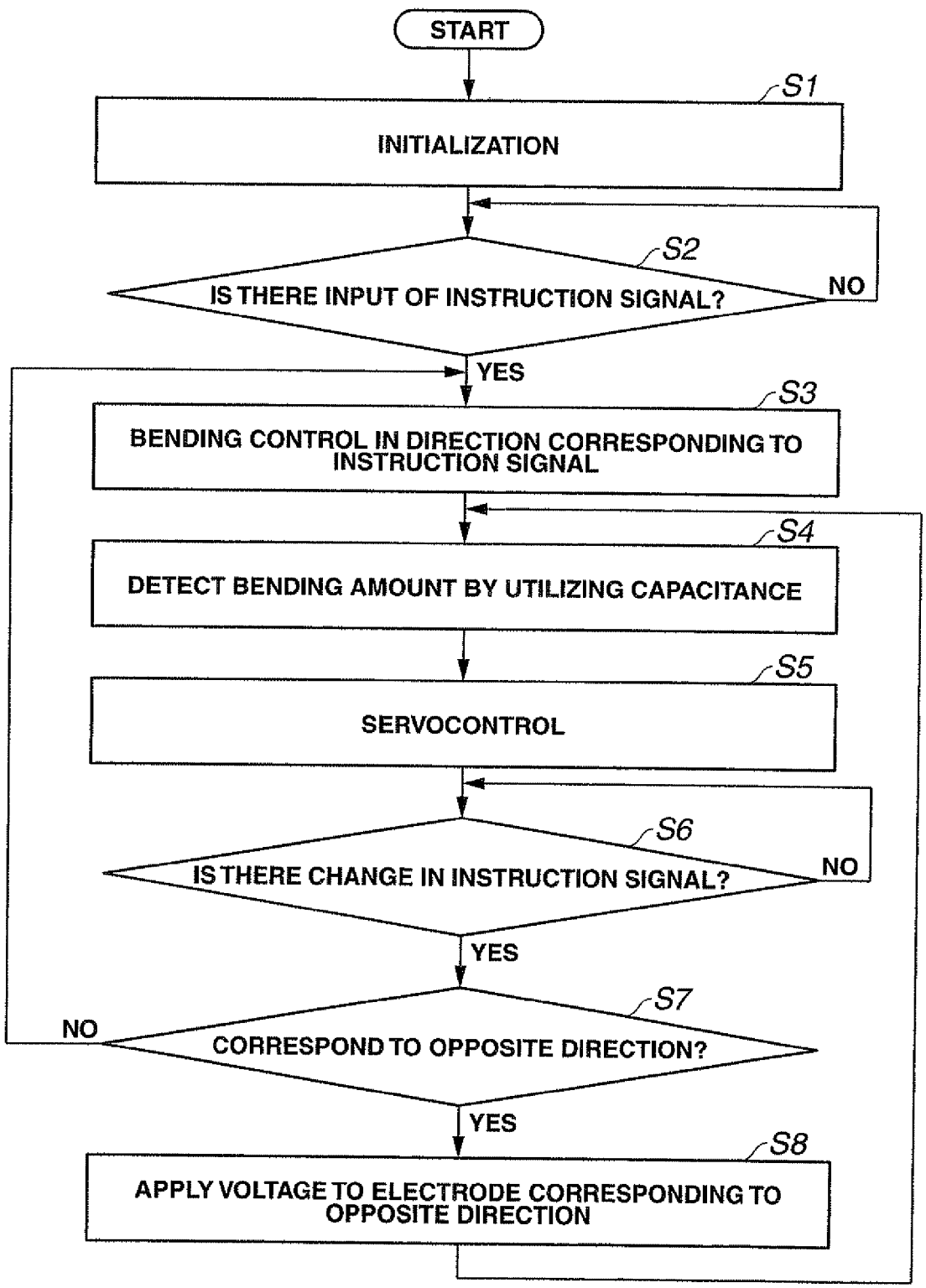
FIG. 11 is a flowchart diagram of an action of the first embodiment.
Figure 12:
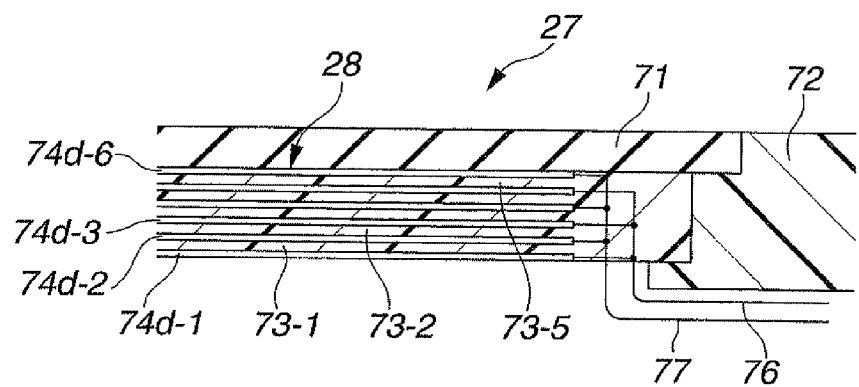
FIG. 12 is a cross-sectional diagram showing a part of an EPAM actuator in a modified example.

Moreover, FIG. 6 shows a schematic configuration of a bending control mechanism part according to the first embodiment; FIG. 7 shows a more detailed configuration of FIG. 6; FIG. 8 shows a specific configuration of FIG. 7; FIG. 9 shows a timing chart describing an action of the bending control mechanism of FIG. 6; FIGS. 10A and 10B are explanatory diagrams showing a comparison of an action in a case where the responsiveness according to the first embodiment is improved and that in a case where the responsiveness is not improved; in which FIG. 10A shows the case where the responsiveness according to the first embodiment is improved; FIG. 10B shows the case where the responsiveness according to the first embodiment is not improved; FIG. 11 shows a flowchart of an action of the first embodiment; and FIG. 12 shows a part of an EPAM actuator in a modified example.

As shown in FIG. 1, an endoscope system 1 provided with the first embodiment of the present invention includes: a flexible endoscope (also referred to as a scope) 3 of the first embodiment, which is inserted into a body of a patient not shown lying on an inspection bed 2 to perform an endoscope inspection; air/water feeding and suction unit (hereinafter abbreviated as an AWS unit) 4 having air/water feeding and suction functions, to which the endoscope 3 is connected; an endoscope system control apparatus 5 for performing a signal processing with respect to an image pickup device incorporated in the endoscope 3, a control processing, a video processing and the like with respect to various kinds of operation means provided to the endoscope 3; and an observation monitor 6 configured of a liquid crystal monitor and the like for displaying video signal generated by the endoscope system control apparatus 5. Note that the observation monitor 6 is provided with a touch panel 33.

Furthermore, the endoscope system 1 includes: an image recording unit 7 for filing, for example, digital video signals generated by the endoscope system control apparatus 5; and a UPD coil unit 8 for displaying a shape of an insertion portion of the endoscope 3 by detecting a position of each position detection coil (hereinafter abbreviated as UPD coil) through reception of a magnetic field by each UPD coil, when the UPD coil unit 8 is connected to the AWS unit 4 and the UPD coils are incorporated in the insertion portion of the endoscope 3.

In FIG. 1, the UPD coil unit 8 is so provided as to be embedded on an upper surface of the inspection bed 2. Then, the UPD coil unit 8 is connected with the AWS unit 4 by a cable 8a.

In addition, in the first embodiment, a housing concave portion is formed at one end portion in a longitudinal direction of the inspection bed 2 and the lower portion thereof so as to house a tray conveying trolley 38. On an upper portion of the tray conveying trolley 38 is mounted a scope tray 39 for housing the endoscope 3 having a watertight structure.

The scope tray 39 housing the sterilized or disinfected endoscope 3 can be conveyed by the tray conveying trolley 38 and housed in the housing concave portion of the inspection bed 2. An operator can pull the endoscope 3 out from the scope tray 39 to use for endoscope inspection, and after the endoscope inspection, the operator has only to house the endoscope 3 in the scope tray 39. After that, the scope tray 39 in which the endoscope 3 after use is housed is conveyed by the tray conveying trolley 38, thereby allowing smooth sterilization or disinfection.

In addition, the AWS unit 4 and the endoscope system control apparatus 5 shown in FIG. 1 transmit and receive information (data) by wireless each other in the first embodiment. Note that, though the endoscope 3 is connected with the AWS unit 4 by a tube unit 19 in FIG. 1, the endoscope 3 and the AWS unit 4 transmit and receive (bi-directionally transmit) information (data) by wireless, as describe later. Moreover, also the endoscope system control apparatus 5 transmits and receives information by wireless each other with the endoscope 3 and the AWS unit 4.

Furthermore, as shown in FIG. 1, the endoscope 3 of the first embodiment includes an endoscope main body 18 and, for example the throwaway type (disposable type) tube unit 19 detachably connected to the endoscope main body 18.

The endoscope main body 18 includes an elongated and flexible insertion portion 21 to be inserted into a body cavity, and an operation portion 22 provided at a rear end of the insertion portion 21. To the operation portion 22, a proximal end of the tube unit 19 is detachably connected.

In addition, to a distal end portion 24 of the insertion portion 21 is disposed, as an image pickup device, an image pickup unit having a charge coupled device (abbreviated as CCD) 25 which makes gain variable in the image pickup device.

In addition, at a rear end of the distal end portion 24 is provided a bending portion 27 bendable with a small amount of force, and the bending portion 27 can be bent by operating a track ball 69 as bending amount instruction means 81 (see FIG. 6) provided to the operation portion 22. The track ball 69 is also used for angle operation (bending operation) and change setting of the functions of other scope switches, for example, settings of angle sensitivity, air-feeding amount and the like.

Furthermore, the insertion portion 21 includes rigidity varying portions, which are provided with rigidity varying actuators 54A, 54B for varying rigidity, formed at a plurality of locations, thereby allowing a smooth insertion operation and the like.

In the first embodiment, the AWS unit 4 and the endoscope system control apparatus 5 transmit and receive data each other by wireless transmission/reception units 177, 101, as shown in FIG. 3, for example. In addition, the observation monitor 6 is connected to a monitor connector 35 of the endoscope system control apparatus 5 by a monitor cable.

Note that, the endoscope system control apparatus 5 includes a power source unit 100, a transmission/reception unit 101 to which electric power is supplied from the power source unit 100, an image processing unit 116 for performing an image processing, and a system control unit 117 for controlling the whole system. The transmission/reception unit 101 is connected to an antenna portion 101a.

In addition, the AWS unit 4 includes a power source unit 175, a transmission/reception unit 177 to which electric power is supplied from the power source unit 175, a UPD unit 176 for generating image data of a shape of insertion portion (UPD image) of the endoscope 3 detected by using the UPD coil unit 8, and an AWS unit 66 for performing AWS control. The transmission/reception unit 177 is connected to the antenna portion 177a.

Then, as described later, image data picked up by the CCD 25 and the image data of the UPD image are transmitted from the endoscope 3 and the AWS unit 4, respectively, to the endoscope system control apparatus 5. Therefore, the endoscope system control apparatus 5 transmits to the observation monitor 6 the video signals corresponding to these image data to allow the UPD image to be displayed together with the endoscope image on a display screen of the monitor.

The observation monitor 6 is configured of a high definition TV (HDTV) monitor so as to be thus capable of displaying a plurality of kinds of images on the display screen concurrently.

In addition, as shown in FIG. 1, for example, the AWS unit 4 is provided with a scope connector 40. To the scope connector 40, the scope connector 41 of the endoscope 3 is detachably connected.

In this case, the scope connector 40 on the AWS unit 4 side is provided with an AWS adapter 42 having a structure allowing not only the connector 41 located on an end portion of the tube unit 19 including only a duct as in the case of the endoscope 3 of the first embodiment but also a connector (illustration abbreviated) in a case where a signal line is inserted through the tube unit 19 to be connectable (see FIG. 3).

Next, a specific configuration of the endoscope 3 according to the first embodiment of the present invention is described with reference to FIG. 2.

As was described of the schematic configuration in FIG. 1, the flexible endoscope 3 includes the endoscope main body 18 having the elongated and flexible insertion portion 21 and the operation portion 22 provided at the rear end of the insertion portion, and the throwaway type (disposable type) tube unit 19 of which proximal end connector portion 52 is detachably connected to a connector 51 for connecting the tube unit which is provided in the vicinity of the proximal end (front end) of the operation portion 22 of the endoscope main body 18.

The tube unit 19 has at a tail end thereof the above-described scope connector 41 detachably connected to the AWS unit 4.

The insertion portion 21 includes the rigid distal end portion 24 provided at the distal end of the insertion portion 21, a bendable bending portion 27 provided at a rear end of the distal end portion 24, and an elongated flexible portion (coiled portion) 53 extended from a rear end of the bending portion 27 to the operation portion 22.

At a plurality of locations, specifically at two locations, on the way along the flexible portion 53, there are provided rigidity varying actuators 54A and 54B, formed of electroactive polymer artificial muscles (hereinafter abbreviated as EPAM) that can be extended/contracted and also varied in rigidity by application of a voltage.

Inside an illumination window provided at the distal end portion 24 of the insertion portion 21, as illumination means, a light-emitting diode (hereinafter abbreviated as an LED) 56 is mounted, for example. The illumination light by the LED 56 is emitted forward through an illumination lens integrally mounted to the LED 56, and illuminates a subject such as a diseased part. Note that a light-emitting element forming the illumination means is not limited to the LED 56, the illumination means can be formed by LD (laser diode) and the like.

In addition, an objective lens is mounted to an observation window provided adjacent to the illumination window, and the CCD 25 having a variable-gain function incorporated therein is disposed at an image-forming position of the objective lens, thereby forming image pickup means for picking up an image of a subject.

Signal lines inserted through the insertion portion 21 with one ends thereof connected to the LED 56 and the CCD 25, respectively, are connected to a centralized control circuit 57 which is provided inside the operation portion 22 and performs a centralized control processing (intensive control processing).

Furthermore, a plurality of UPD coils 58 are disposed at predetermined intervals in the insertion portion 21 along the longitudinal direction thereof. The signal line connected to each of the UPD coils 58 is connected to the centralized control circuit 57 via a UPD coil drive unit 59 provided in the operation portion 22.

Moreover, at four locations in a circumferential direction inside of an outer coat of the bending portion 27, there is each disposed EPAM actuator 28 as an angle element (bending element) formed by disposing EPAM in the longitudinal direction. The EPAM actuator 28 and the rigidity varying actuator 54A, 54B are connected to the centralized control circuit 57 via the signal lines, respectively.

In the centralized control circuit 57 is provided a bending control mechanism 70 for performing bending control to be described later.

The EPAM used for the EPAM actuator 28 and the rigidity varying actuators 54A, 54B, has electrodes mounted on both plate-like surfaces thereof, for example, and a voltage is applied to the electrodes, thereby allowing to be contracted in a thickness direction and extended in a longitudinal direction. Note that the EPAM can vary a deformation amount in proportion to approximately square of the voltage to be applied, for example.

The EPAM can vary the rigidity thereof by extension or contraction, so that the rigidity varying actuators 54A, 54B can vary the rigidity thereof by utilizing the function of the EPAM.

In addition, an air/water feeding duct 60a and a suction duct 61a are inserted through the insertion portion 21, and the rear end of the insertion portion 21 serves as a connector portion 51 open in the vicinity of the front end of the operation portion 22. To the connector portion 51, a connector portion 52 provided to the proximal end of the tube unit 19 is detachably connected.

Then the air/water feeding duct 60a is connected to an air/water feeding duct 60b inserted through the tube unit 19. The suction duct 61a is connected to a suction duct 61b inserted through the tube unit 19 and is diverged in the connector portion 52 to open outside, and is communicated with an insertion port (also referred to as a forceps port) 62 into which treatment instruments such as forceps are insertable. The forceps port 62 is closed with a forceps tap 62a when not in use.

Rear ends of the air/water feeding duct 60b and the suction duct 61b serve as an air/water feeding cap 63 and a suction cap 64 in the scope connector 41, respectively.

The air/water feeding cap 63 and the suction cap 64 are connected to an air/water feeding cap and a suction cap of the AWS adapter 42 shown in FIG. 3, respectively. Inside of the AWS adapter 42, the air/water feeding cap is diverged into the air feeding duct and the water feeding duct, and the air feeding duct is connected to an air feeding pump 65 in the AWS unit 4 with an electromagnetic valve B1 interposed, and the water feeding duct is connected to a water feeding tank 48. Also the water feeding tank 48 is connected to the air feeding pump 65 with an electromagnetic valve B2 interposed in the midway.

The air feeding pump 65 and the electromagnetic valves B1, B2 are connected to an AWS control unit 66 by a control line (drive line), and controlled to open and close by the AWS control unit 66, thereby allowing air feeding and water feeding. Note that the AWS control unit 66 also performs control of suction action by controlling to open and close a pinch valve 45.

As shown in FIG. 1 and FIG. 2, a grasping portion 68 for an operator to grasp is provided to the operation portion 22 of the endoscope main body 18. In the present embodiment, as shown in FIG. 1, the grasping portion 68 is formed with a side surface portion of a cylindrical shape body, for example, in the vicinity of a rear end (proximal end) (which is opposite side of the insertion portion 21 side) of the operation portion 22.

The grasping portion 68 includes, at a periphery portion including the grasping portion 68 itself; for example three scope switches SW1, SW2, and SW3 for performing remote-control operation such as release, freeze, and the like, provided along an axis in a longitudinal direction of the grasping portion 68, and the scope switches are each connected to the centralized control circuit 57 (see FIG. 2).

The proximal end surface Sa (also referred as a top end surface since the proximal end side is normally set to come to the top and used for endoscope inspection as in FIG. 1 or FIG. 2) provided in the rear end (proximal end) of the grasping portion 68 (or operation portion 22) forms an inclined surface, and at a position on the inclined surface which is opposite side of the position where the scope switches SW1, SW2, and SW3 are provided, there is provided the waterproof-structured track ball 69 for performing angle operation (bending operation) and setting and the like of other remote control operations switching from the angle operation. Note that the waterproof structure in this case is such that, in fact, a side of an encoder for rotatably holding the track ball 69 or detecting a rotation amount thereof is covered with waterproof film and the track ball 69 is rotatably held on outside of the film.

Furthermore, on both sides of the track ball 69 disposed on the inclined surface, an air/water feeding switch SW4 and a suction switch SW5 are symmetrically disposed.

The track ball 69 and the scope switches SW4, SW5 are also connected to the centralized control circuit 57.

In addition, as shown in FIG. 2, the endoscope 3 of the present embodiment, for example, has inside in the vicinity of the rear end of the operation portion 22 an antenna portion 141 by which signal data is transmitted and received, and also has in the operation portion 22 a battery 151 and a charging circuit 152 connected to the battery 151, and non-contact charging coil 153.

Therefore, the connector portion 51 of the operation portion 22 of the first embodiment is formed only by a duct connector portion composed of an air/water feeding connector and a suction connector.

The tube unit 19 detachably connected to the endoscope main body 18 of the first embodiment eliminates a signal line required to be inserted through an existing universal cable and has a structure in which duct tubes of the air/water feeding duct 60 and the suction duct 61.

The above-described battery 151 is a rechargeable secondary battery such as a lithium battery. The battery 151 is connected with the watertight-structured non-contact charging coil 153 incorporated in a part in the vicinity of outer surface of the operation portion 22 via the charging circuit 152. On the outer surface of the part in which the non-contact charging coil 153 is incorporated, a non-contact power feeding coil, not shown, provided in an external apparatus is disposed oppositely and alternating current is supplied to the non-contact power feeding coil, thereby allowing the battery 151 to be charged.

That is, alternating current power is supplied to the non-contact power feeding coil disposed on the outer surface side of the operation portion 22, thereby non-contactly transmitting the alternating current power by electromagnetic coupling to the non-contact charging coil 153 in the operation portion 22. The alternating current power is converted into direct current voltage for charging the battery 151 by the charging circuit 152, to be supplied to the battery 151, thereby allowing the battery 151 to be charged.

In the first embodiment, the LED 56 is adopted as the illumination means, so that power consumption can be greatly reduced, compared with a case where a lamp is used. Also, an ultra-sensitive CCD 25 (having the variable gain function incorporated therein) is adopted as the image pickup device, so that a bright image having a high S/N ratio can be obtained even in a state where illumination light amount is small.

Therefore, even in a case where the battery 151 is adopted, the endoscope inspection can be performed for much longer hours, compared with the conventional example. In addition, as the battery 151, a smaller and lighter battery than one in the conventional example can be adopted, thereby reducing the weight of the operation portion 22 and allowing excellent operability to be secured.

With the first embodiment, the tube unit 19 is composed only of a duct system, so that the tube unit 19 has a configuration more suitable for the throwaway type. Also when recycling (reusing), it is easier to recycle the tube unit 19, because the tube unit 19 does not have electric cables inside.

When the duct system is not in use, the endoscope can be used by detaching the tube unit 19 from the endoscope main body 18. That is, the tube unit 19 is not necessary in this case, thereby preventing the tube unit 19 from getting in the way of operation and improving the operability. In addition, the duct system of the endoscope main body 18 can be reduced in length, so that cleaning and the like can be performed in a short time.

Thus, the configuration with improved operability and cleanability is realized by detachably providing to the endoscope main body 18 the tube unit 19 having only the duct system inserted therethrough.

FIG. 4 shows an inner configuration of the distal end side of the endoscope 3 of the first embodiment, and FIG. 5 shows a cross section taken along A-A line of FIG. 4. The distal end portion 24 of the insertion portion 21 has an objective lens 23 mounted to the observation window provided, for example in the vicinity of the center of the distal end portion 24, and the CCD 25 at an image-forming position of the objective lens 23.

To the illumination windows provided, for example, at two positions adjacent to the observation window, the LEDS 56 for generating white light, as illumination means, are integrally mounted with lenses. Also the air/water feeding duct 60b and the suction duct 61b are provided adjacent to the observation window.

To the rear end of the distal end portion 24 is fixed a distal end of a rubber tube 71 having moderate flexibility which forms the outer coat of the bending portion 27, while a rear end of the rubber tube 71 is joined to a distal end of an outer coat tube 72 of the flexible portion 53.

The cylindrically-shaped EPAM actuator 28 is disposed on an inner side of the rubber tube 71. The distal end of the cylindrically-shaped EPAM actuator 28 is fixed to the distal end portion 24, while the rear end of the EPAM actuator 28 is fitted in and fixed to a concave portion of the outer coat tube 72.

The cylindrically-shaped EPAM actuator 28 includes: a cylindrically-shaped EPAM 73; electrodes 74u, 74d, 74l, and 74r for bending in upward, downward, leftward, and rightward directions, which are disposed at four positions respectively corresponding to down, up, right, and left of the inner circumferential surface of the cylindrically-shaped EPAM 73; and four electrodes 75 provided on an outer circumferential surface at positions opposed respectively to those of the electrodes 74u, 74d, 74l and 74r.

Note that, in FIG. 4, the upper side of the paper surface is upper side of the bending direction. As the EPAM actuator 28 of the first embodiment, those having a characteristics of extending in a planar direction by applying voltage are adopted, so that when bending the EPAM actuator in upward direction, for example, driving voltage is applied to the electrode 74*u* provided in the downward direction opposite to the upward direction and the electrode 75 (positioned opposing to the electrode 74*u*). In addition, the four electrodes 75 on the outer circumferential surface may be an electrode provided on the whole surface.

Note that the rubber tube 71 provided outside of the EPAM actuator 28 has a function such that a restoring force tending to return to an non-bending straight state acts by an elastic force when the EPAM actuator 28 is displaced and bent. In order to increase the restoring force, a coil spring may be disposed on the inner circumferential side of the EPAM actuator 28, for example.

In addition, the electrodes 74*u*, 74*d*, 74*l*, and 74*r* and electrodes 75 transmit drive signals for driving the EPAM actuator 28, and connected to the bending control mechanism 70 shown in FIG. 6 via signal lines 76, 77 for transmitting signals corresponding to displacement amounts. In FIG. 6, the electrodes 74*u*, 74*d* and electrodes 75 are connected to EPAM drive means 78*u*, EPAM drive means 78*d*, displacement amount detection means 79*u*, and displacement detection means 79*d* in the bending control mechanism 70 related to the upward and downward directions.

Note that, in FIG. 6, though only the bending control mechanism 70 related to the upward and downward directions is shown for simplification, the bending control mechanism related to the leftward and rightward directions is also provided in fact.

The EPAM drive means 78*u*, 78*d* which output an EPAM drive signal in the upward and downward directions, and the displacement amount detection means 79*u*, 79*d* which detect the displacement amount of the EPAM in the upward and downward directions are connected to bending amount control means 80. The bending amount control means 80 controls the drive actions by the EPAM drive means 78*u*, 78*d* in response to the bending amount instruction operation by the bending amount instruction means 81 configured of the track ball 69. In this case, the bending amount control means 80 controls the drive actions of the EPAM drive means 78*u*, 78*d* according to the displacement amount of EPAM in the upward and downward directions to be detected by the displacement amount detection means 79*u*, 79*d*.

In the first embodiment, the bending amount control means 80 monitors an instruction signal of bending amount from the bending amount instruction means 81, as described later, and when bending instruction from non-bending straight direction (also referred to as a reference direction) to a predetermined direction is given, the bending amount control means 80 performs bending control according to the bending instruction. The bending amount control means 80 incorporates therein an inversion instruction detection means 80*a* for detecting an inversion instruction signal for bending the EPAM actuator in a direction returning from the bending direction at that time to the reference direction, that is, in a direction opposite to the last bending direction (reverse direction). When detecting the instruction signal to bend the EPAM actuator in the opposite direction, the bending amount control means 80 performs bending control in response to the instruction operation.

Note that, as for the instruction signal of bending amount by the bending amount instruction means 81, in a case where the track ball 69 is used, the direction in which the track ball 69 rotates corresponds to the bending direction and the rotation amount of the track ball 69 corresponds to the instruction amount of the bending amount (bending angle). In this case, orthogonally disposed two rotary encoders and the like detect the bending direction and bending amount. Note that, instead of the track ball 69, a joystick, mouse, or cross pad may be adopted as the bending amount instruction means 81.

FIG. 7 shows a more specific configuration of FIG. 6, and FIG. 8 shows a circuit configuration realizing the configuration in FIG. 7. As shown in FIG. 7, the instruction signal of bending amount by the bending amount instruction means 81 is inputted to the bending amount control means 80 similarly as in the configuration in FIG. 6.

The bending amount control means 80, in response to the instruction signal of bending amount, controls high voltage application by high-voltage applying means 83*i* equivalent to the EPAM drive means 78*u*, 78*d* in FIG. 6. Note that in FIG. 8, in fact, 83*i* to 86*i* are provided corresponding to four directions, respectively. For example, the high-voltage applying means 83*i* represents one of high-voltage applying means for upward bending 83*u*, high-voltage applying means for downward bending 83*d*, high-voltage applying means for leftward bending 83*l*, and high-voltage applying means for rightward bending 83*r*.

The high-voltage applying means 83*i* applies high voltage to an electrode 74*i* of the EPAM actuator 28 via an overcurrent limiting means 84*i* which prevents overcurrent from being generated by limiting (regulating) the flow of overcurrent equal to or higher than a predetermined current value, to displace the EPAM actuator 28 so as to bend in an instructed direction.

In addition, the displacement amount of the EPAM actuator 28 is detected by measuring capacitance changing in accordance with the displacement by capacitance measuring means 85*i* equivalent to the displacement amount detection means 79*u*, 79*d* in FIG. 6. That is, by measuring the capacitance, the displacement amount is detected.

A capacitance measurement value measured (detected) by the capacitance measuring means 85*i* is inputted to the bending amount control means 80. The bending amount control means 80 controls high-voltage application by the high-voltage applying means 83*i* such that the measured capacitance measurement value becomes a value coincident with the bending direction and bending amount instructed by the bending amount instruction means 81.

Moreover, the EPAM actuator 28 in the first embodiment has characteristics close to those of a capacitor having a high insulation resistance value, and is connected to discharge means 86*i* for discharging electric charge conserved in the capacitor in order to improve responsiveness. The discharge means 86*i* is actually formed by a resistor Rb for discharge, as shown in FIG. 8.

Next, a specific configuration of an electric circuit system realizing FIG. 7 is described with reference to FIG. 8.

The instruction signal by the bending amount instruction means 81 is inputted not only to a control circuit 90 configured of a CPU, for example, which is included in the bending amount control means 80, but also to the inversion instruction detection circuit 91 equivalent to the inversion instruction detection means 80*a*. The instruction signal by the bending amount instruction means 81 is a signal including the bending direction, and the bending amount with respect to the bending direction. The inversion instruction detection circuit 91 monitors the instruction signal, and when detecting the inverted instruction signal (from the previous instruction signal) instructing to return the bending direction based on the last instruction signal to the reference direction, the inversion instruction detection circuit 91 outputs the inversion detection signal to the control circuit 90.

The control circuit 90 normally controls the high-voltage application action by the high-voltage applying means 83i in the bending direction in the instruction signal in response to the instruction signal. However, when the inversion detection signal is inputted, the control circuit 90 improves a response speed by performing control for applying a high voltage of polarity for bending the EPAM actuator in the direction reverse to the bending direction based on the last instruction signal.

As shown in FIG. 8, the high-voltage applying means 83i includes: a switching circuit 92 for generating a switching voltage by a switching device not shown; a step-up transformer 93 for generating a stepped-up high voltage on a secondary winding as a result of switching voltage application to a primary winding; a measuring reference signal generating circuit 94 for applying a measuring reference signal to a second primary winding in the step-up transformer 93; a rectifying and smoothing circuit 95 for rectification and smoothing, which is connected to the secondary winding of the step-up transformer 93; and a constant-voltage circuit 96 for controlling a voltage such that a voltage outputted from the rectifying and smoothing circuit 95 becomes a constant voltage. Note that the reference symbol F shown by a dotted line in FIG. 8 is a filter for bypassing the measuring reference signal.

The control circuit 90 applies a duty control signal to the switching circuit 92 in response to the instruction signal, and controls the power supplied to the rectifying and smoothing circuit 95 side via the step-up transformer 93. In addition, the control circuit 90 applies a synchronization signal to the measuring reference signal generating circuit 94 to generate a measuring reference signal from the measuring reference signal generating circuit 94 in synchronization with the synchronization signal.

A direct-current voltage outputted from one output terminal of the constant-voltage circuit 96 is applied to the electrode (for example, one electrode 74i) of the EPAM actuator 28 through a current limiting resistor Ra configuring the overcurrent limiting means 84i.

To the halfway of the signal line 77 connecting the other output terminal (ground) of the constant-voltage circuit 96 and the electrode 75 of the EPAM actuator 28, is connected a primary winding of a step-down transformer 97 configuring the capacitance measuring means 85i, and to a secondary winding of which voltage is stepped down by the step-down transformer 97 is connected a filter circuit 98 having a characteristics of band-pass filter for passing frequency of the measuring reference signal. Then, the measuring reference signal is extracted by the filter circuit 98 to be inputted to a root-mean-square value detection circuit (abbreviated as RMS detection circuit in the drawings) 99.

The root-mean-square value detection circuit 99 calculates the root-mean-square value of the voltage of the detected measuring reference signal, to output to the control circuit 90 the measuring reference value as a detection signal.

The EPAM actuator 28 is displaced so as to be extended by voltage application, thereby the capacitance between electrodes is changed. Then the change of the capacitance results in a change in impedance with respect to the measuring reference signal, and the root-mean-square value to be detected by the root-mean-square value detection circuit 99 changes in accordance with the displacement amount, that is, the bending amount of the EPAM actuator 28.

The control circuit 90 performs control by calculating a bending amount from the root-mean-square value detected in synchronization with the synchronization signal and changing a duty value of a duty control signal to be applied to the switching circuit 92 such that the detected bending amount coincides with the bending amount based on the instruction signal.

Description is made below on an action in a case where bending instruction operation is performed in the endoscope 3 of the first embodiment configured as such. In order to make it easier to understand a fundamental action according to the first embodiment, description is made on the action in a case where the bending portion is bent in an upward direction (abbreviated as UP in FIG. 6) and in a downward direction (abbreviated as DOWN in FIG. 6) as shown in FIG. 6, with reference to FIG. 9 showing the action timing.

The bending amount instruction means 81 is operated to perform operation to bend the EPAM actuator 28 in the upward direction from the time t1 to t2 in FIG. 9, for example, and bending amount instruction information in the upward direction (in the instruction signal) in the case is changed as shown in (A) of FIG. 9.

In this case, the bending amount control means 80 performs drive control of the EPAM drive means 78u in order to bend the EPAM actuator in the upward direction as substantially following the bending amount instruction information. The EPAM drive means 78u applies the voltage (potential) shown in (C) of FIG. 9 to the electrode 74u.

Accordingly, the displace amount (of the EPAM actuator 28) of the bending portion 27 changes as shown in (B) of FIG. 9.

After bending the EPAM actuator in the upward direction, in order to cancel the bending in the upward direction, the bending amount instruction means 81 is operated to perform operation to bend the EPAM actuator in the downward direction reverse to the upward direction to bring the EPAM actuator into a straight direction, for example (from the time t2 to t3). When this operation is performed, the inversion instruction detection means 80a in the bending amount control means 80 detects bending instruction in an opposite direction. Then, in response to the detection, the bending amount control means 80 performs drive control for bending the EPAM actuator in the downward direction as shown in (D) of FIG. 9.

That is, in order to quickly (with sufficient responsiveness) cancel the bending in the upward direction, the bending amount control means 80 performs drive control of the EPAM drive means 78d in the downward direction, and the EPAM drive means 78d applies the voltage (potential) shown in (D) of FIG. 9 to the electrode 74d.

Such a configuration allows the response speed to be improved as shown by the solid line in (B) of FIG. 9.

Note that, when control action to drive and bend the EPAM actuator in the opposite direction is not thus performed by using the detection result by the inversion instruction detection means 80a, voltage to be applied is not outputted during from the t2 to t3 in (D) of FIG. 9 as shown by the dotted line.

In this case, the displacement amount is as shown by the dotted line in (B) of FIG. 9, and the response speed decreases compared with the case shown by the solid line.

In addition, after the operation of returning the EPAM actuator to the straight direction, if a user performs bending amount instruction operation in the downward direction from the time t4 to t5, and performs bending amount instruction operation to return the EPAM actuator to the straight direction from the time t5 to t6 as shown in (A) of FIG. 9, the bending amount control means 80 performs drive control as shown in (D) and (C) of FIG. 9 in that case.

Moreover, the user performs bending amount instruction operation in upward direction from the time t7 to t8 and performs bending amount instruction operation to return the EPAM actuator to the straight direction from the time t8 to t9, the bending amount control means 80 performs drive control as shown in (C) and (D) of FIG. 9 in that case.

The control action from the time t7 to t9 is the same as that from the time t1 to t3 except that the instruction value of the bending amount is increased.

Also in this case, from the time t8 to t9, the bending instruction operation in the opposite direction is detected and bending drive control in the opposite direction is performed, so that the response speed is improved compared with the case, shown by the dotted line, where such a bending drive control is not performed.

The control action from the time t4 to t6 is the same as that from the time t7 to t9 except that the bending direction is reverse. Also in this case, from the time t5 to t6, the bending instruction operation in the opposite direction is detected and bending drive control in the opposite direction is performed, so that the response speed is more improved than in the case, shown by the dotted line, where such a bending drive control is not performed.

FIGS. 10A and 10B are action explanatory diagrams in which action in a case where the bending instruction operation in the opposite direction is detected to improve the response speed is compared with that in a case where the response speed is not improved.

FIG. 10A schematically shows the action of the first configuration, for example, from the time t1 to t3 in FIG. 9. FIG. 10B schematically shows the action, for example, from the t1 to t3 in FIG. 9 in a case where the bending drive control in the opposite direction is not performed. The left sides in FIGS. 10A and 10B show a state where voltage is applied to the electrode 74*u* for upward bending based on the bending instruction. The EPAM on the electrode 74*u* side extends by the voltage application as shown by arrow sign A1. At this time, due to the extension of the EPAM on the electrode 74*u* side, the EPAM on the electrode 74*d* side is contracted as shown by the arrow sign A2. The action in this case is the same in FIG. 10A and FIG. 10B.

The right sides in FIGS. 10A and 10B show the action in the case where the bending instruction operation to return the EPAM actuator bent in the upward direction to the straight direction is then performed.

In the case of FIG. 10B, the voltage to be applied is stopped, so that the EPAM actuator recovers (returns) to the original direction by the restoring forces of the EPAM actuator 28, the rubber tube 71, and the like. When the voltage application is stopped, the EPAM on the electrode 74*u* side tries to return to the original direction as shown by arrow sign A3. At this time, also the EPAM on the electrode 74*d* side tries to return to the original direction as shown by the arrow sign A4.

On the contrary, in a case of FIG. 10A, the EPAM on the electrode 74*d* side is further applied with voltage to be driven such that the lower direction side thereof is extended, thereby enabling the EPAM to more quickly return to the original direction. When the voltage application is stopped, the EPAM on the electrode 74*u* side tries to return to the original direction as shown by the arrow sign A3. At this time, by applying voltage, the EPAM on the electrode 74*d* side is extended and tries to quickly return to the original direction as shown by the arrow sign A5.

FIG. 11 shows a flowchart of control content in a case where the bending instruction operation according to the first embodiment is performed.

When power is turned on to be in an action state, the control circuit 90 performs initial setting as shown in Step S1. For example, the control circuit 90 performs the settings of a threshold value Vth when detecting the inversion detection signal by the inversion instruction detection circuit 91 and a maximum angle θ when regarding the bending direction as the opposite direction. In addition, in a case where the bending amount instruction means 81 is the track ball 69 or the like, the position data in the state of initial setting is set as the state where the bending amount is zero (straight state).

After the initial setting processing, the control circuit 90 monitors the instruction signal from the bending amount instruction means 81 to go into an instruction signal input waiting state, as shown in Step S2.

Then, when the bending instruction operation is performed by the bending amount instruction means 81, the instruction signal corresponding to the operation is inputted to the control circuit 90. Then, as shown in Step S3, the control circuit 90 outputs to the high-voltage applying means 83*i* in a bending direction corresponding to the instruction signal the control signal (duty control signal in FIG. 8) corresponding to the bending instruction amount of the bending direction, to bend the EPAM actuator 28 in the direction corresponding to the instruction signal.

At that time, the capacitance measuring means 85*i* measures the root-mean-square value of the measuring reference signal applied to the side of the EPAM actuator 28 series-connected with the resistor Ra with a constant value by utilizing the capacitance change along with the bending of the EPAM actuator 28, and outputs a detection signal corresponding to the bending amount to the control circuit 90 as shown in Step S4.

Then, as shown in Step S5, the control circuit 90 detects a difference value between the detection signal and the instruction amount to perform servocontrol such that the difference value becomes not more than a predetermined value.

After that, as shown in Step S6, the control circuit 90 goes into an instruction signal change waiting state. When bending instruction operation is performed by the bending amount instruction means 81, the inversion instruction detection circuit 91 of the control circuit 90 judges whether or not the bending direction based on the last instruction signal is equivalent to a direction based on the instruction signal when the operation is performed so as to return the EPAM actuator to the opposite direction, as shown in Step S7. That is, when the value of instruction signal of the operation for returning the EPAM actuator to the opposite direction is equal to or larger than the threshold value Vth, the inversion instruction detection circuit 91 judges that instruction signal of the opposite direction has been detected. When the value is smaller than the threshold value Vth, the inversion instruction detection circuit 91 judges that the signal has not been detected.

When it is judged that the instruction signal of the opposite direction has been detected, the control circuit 90 applies the voltage from the high-voltage applying means 83*i* to the electrode corresponding to the opposite direction (so as to bend the EPAM actuator 28 in the opposite direction), as shown in Step S8. The voltage value to be applied in this case is determined as shown in FIG. 9, for example.

That is, as shown at A in FIG. 9, in a case where the bending instruction information based on which the EPAM actuator is bent in a certain direction is changed in a direction in which the voltage value decreases from a peak value in order to return the EPAM actuator to the straight state, the voltage value proportional to the peak value is applied as an initial value to the electrode in the opposite direction, and the voltage value to be applied is changed according to magnitude of the bending instruction value.

After that, returning to the processing in Step S4, the capacitance measuring means 85*i* measures the root-mean-square value of the measuring reference signal by utilizing the capacitance change along with the bending of the EPAM actuator 28, to output the detection signal corresponding to the bending amount to the control circuit 90.

Then as shown in Step S5, the control circuit 90 detects the difference value between the detection signal and the instruction amount, to perform servocontrol such that the difference value becomes not more than a predetermined value.

On the other hand, in the judgment processing in Step S7, when the instruction signal is not judged to be of the opposite direction, the processing returns to Step S3, and the above-described processings are performed.

Such a bending drive control can realize the bending mechanism whose response speed with respect to the bending operation is satisfactory.

The bending mechanism is formed such that the bending portion 27 is bent by the EPAM actuator 28, so that the bending portion 27 can be simply and easily bent in a desired direction by performing operation for applying a high voltage as a drive signal and the bending mechanism can be reduced in weight. Also, the bending portion can be simply and easily bent in a desired direction by operating the track ball 69 and the like, thereby allowing the bending operability to be improved.

Note that, as a modification example of the EPAM actuator 28 according to the present embodiment, a configuration in which the EPAM main body part 73 and the electrodes are arranged in a laminated manner may be adopted, as partly shown in FIG. 12. That is, the laminated structure is formed in the following order: electrode 74d-1, EPAM main body layer 73-1, electrode 74d-2, EPAM main body layer 73-2, electrode 74d-3, . . . , and electrode 74d-6, and the electrodes 74-d-1, 74d-3, and 74d-5 are connected to the signal line 76, and the electrodes 74d-2, 74d-4, and 74d-6 are connected to the signal line 77.

With such a configuration, the EPAM actuator 28 may be bent by applying lower voltage. In this case, the EPAM actuator 28 can be bent by applying far lower voltage compared with the case in the first embodiment. Note that, though FIG. 12 shows the case of a five-layered configuration, the configuration is not limited thereto.

(Second Embodiment)

Figure 13:
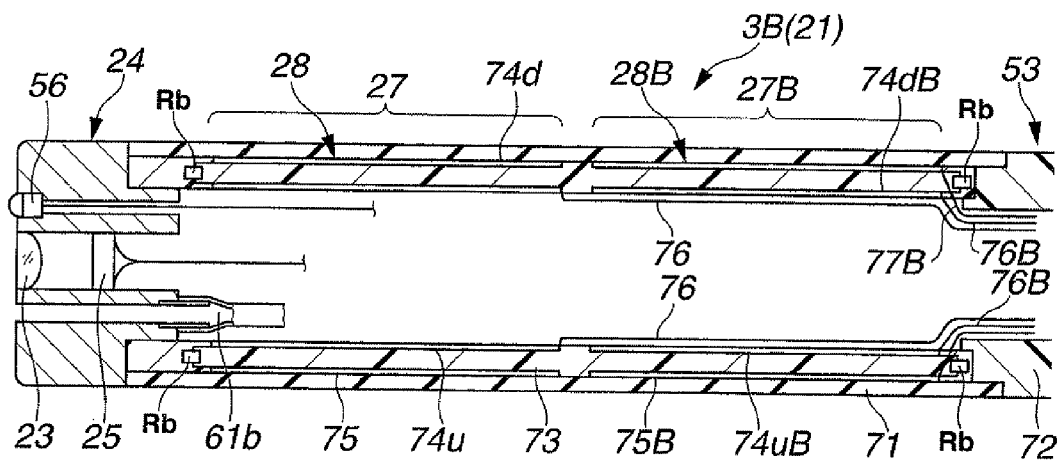
FIG. 13 is a vertical cross-sectional diagram showing an inner configuration of a distal end side of an insertion portion of an endoscope according to a second embodiment of the present invention.

Next, an endoscope according to the second embodiment is described with reference to FIG. 13. The second embodiment is an example of an endoscope in which a plurality of, or two in the present embodiment, bending portions formed with the EPAM actuators are provided in the longitudinal direction of the insertion portion. FIG. 13 shows a configuration of distal end side of an insertion portion 21 of an endoscope 3B according to the second embodiment. Though the bending portion 27 has the EPAM actuators 28 for bending the bending portion in up, down, left, and right directions in the first embodiment as shown in FIG. 4, for example, a second bending portion 27B is further provided on a rear end side of the bending portion 27 in the endoscope 3B according to the second embodiment as shown in FIG. 13.

The second bending portion 27B is formed with an EPAM actuator 28B having, for example, the same configuration as that of the EPAM actuator 28 provided in the bending portion 27. In the example shown in the drawing, the EPAM main body part 73 is formed in common (may be configured separately) for the EPAM actuators 28 and 28B.

Note that, the electrodes and the signal lines on the EPAM actuator 28B side are shown by attaching the symbol B to those of the EPAM actuator 28. For example, the electrode for upward bending and the electrode for downward bending are shown by 74uB and 74dB, respectively, and the signal line connected to these electrodes 74uB, 74dB is shown by 76B, and the signal line connected to the common electrode 75B provided on the outer circumferential side is shown by 77B.

Furthermore, the electrode 75B on the outer circumferential side of the EPAM actuator 28B is electrically conducted to the electrode 75 on the outer circumferential side of the EPAM actuator 28, and these electrodes are conducted to the common signal line 77B.

The electrodes 74uB, 74dB, and the like of the EPAM actuator 28B are connected to a second bending control apparatus, not shown, provided in the operation portion 22 via the signal line 76B, thereby allowing the second bending portion 27B to be bent independently from the bending amount instruction means 81 using a bending amount instruction means configured of a second track ball and the like, not shown, in the second bending control apparatus.

In addition, in the second embodiment, in the vicinity of the distal end of the EPAM actuator 28, for example, resistors Rb configuring the discharge means 86i are connected so as to electrically conduct between the electrodes 74d and 75, and between 74u and 75, respectively. Similarly, also in the EPAM actuator 28B, at a rear end thereof, for example, resistors Rb configuring the discharge means 86i are connected so as to electrically conduct between the electrodes 74dB and 75B, and between 74uB and 75B, respectively. Other configurations are almost the same as those in the first embodiment.

With the second embodiment, the bending portions 27 and 27B, each of which can be bent independently in an arbitrary direction of up, down, left, and right directions, are provided in the vicinity of the rear end of the distal end portion 24 in the longitudinal direction of the insertion portion 21. Therefore, even when the insertion portion 21 is inserted into a curved region in a body cavity, for example, the insertion portion can be bent more greatly than that in the first embodiment, and can be bent also in a different shape, thereby allowing smooth insertion work.

In the above, though description has been made on the configuration in which the EPAM drive means 78u, 78d, and the displacement amount detection means 79u, 79d, and the like in FIG. 6, for example, are incorporated in the endoscopes 3 and 3B, a configuration in which these means are provided outside of the endoscope may be adopted.

The above-described two embodiments can realize the endoscope which is capable of obtaining operability by the actuator using the conductive polymer member, and improving responsiveness when the bending operation is performed.

In addition, configurations in which the above-described embodiments are partly combined or modified also belong to the present invention.

Industrial Applicability

The bending portion provided on the distal end side of the insertion portion is formed with the EPAM actuator and a driving voltage is applied thereto, which enables the bending portion to be driven and bent while obtaining simple and excellent operability.

The invention claimed is:

1. An endoscope comprising:
an insertion portion including a bending portion;
an actuator including a conductive polymer member having a cylindrical shape that extends or contracts according to application of a driving voltage and a plurality of electrodes provided so as to correspond to a plurality of bending directions of the conductive polymer member having a cylindrical shape;
a bending instruction operation portion for outputting, to the actuator, an instruction signal of a bending direction and a bending amount so that the bending portion performs a bending action by an arbitrary amount from a reference direction in which the bending portion is not bent to an arbitrary direction;

a driving voltage applying portion for applying a driving voltage to the actuator in response to an instruction operation of the bending direction by the bending instruction operation portion;

a detection portion for detecting a displacement amount of the actuator by the application of the driving voltage by the driving voltage applying portion;

a control portion configured to perform control to start applying a driving voltage for bending the bending portion in the opposite direction to an electrode disposed at a position opposed to a predetermined electrode of the plurality of electrodes and stop applying a predetermined driving voltage to the predetermined electrode, at a timing of detecting an output of the instruction signal outputted by the bending instruction operation portion for bending the bending portion in an opposite direction to an arbitrary direction after applying the predetermined driving voltage to the predetermined electrode of the plurality of electrodes in response to detection of the instruction signal for causing the bending portion to perform a bending action in the arbitrary direction by an arbitrary amount; and a flexible member provided so as to cover an outside of the actuator, the flexible member being configured to apply a restoring force so as to return the insertion portion to the reference direction when the application of the driving voltage by the driving voltage applying portion stops, wherein the control portion, when detecting the instruction operation for bending the insertion portion in the opposite direction, judges that instruction operation in the opposite direction has performed if an amount of the instruction operation in the opposite direction is equal to or larger than a threshold value set in advance.

2. The endoscope according to claim 1, wherein the detection portion detects the displacement amount by measuring capacitance between electrodes when a driving voltage is applied between the electrodes of the actuator.

3. The endoscope according to claim 1, further comprising a current limiting portion for limiting current flowing to the actuator when a driving voltage is applied to the actuator.

4. The endoscope according to claim 1, further comprising a discharge portion for discharging electric charge between the electrodes of the actuator.

5. The endoscope according to claim 1, wherein the bending portion configured of the actuator is provided in plural numbers in a longitudinal direction of the insertion portion.

* * * * *